(12) United States Patent
Mui et al.

(10) Patent No.: US 9,372,132 B2
(45) Date of Patent: Jun. 21, 2016

(54) BLOOD COMPONENT SAMPLING SYSTEM AND BLOOD PROCESSING SYSTEMS AND METHODS EMPLOYING SAME

(71) Applicant: Fenwal, Inc., Lake Zurich, IL (US)

(72) Inventors: Tat Mui, Chicago, IL (US); Randy Murphey, Pleasant Prarie, WI (US); Daniel Lynn, Spring Grove, IL (US); Richard L. West, Lake Villa, IL (US); Hugo Ramon, Wauconda, IL (US); Shawn Davis, Bristol, WI (US)

(73) Assignee: Fenwal, Inc., Lake Zurich, IL (US)

( * ) Notice: Subject to any disclaimer, the term of this patent is extended or adjusted under 35 U.S.C. 154(b) by 252 days.

(21) Appl. No.: 13/785,160

(22) Filed: Mar. 5, 2013

(65) Prior Publication Data

US 2014/0080113 A1     Mar. 20, 2014

Related U.S. Application Data

(60) Provisional application No. 61/702,924, filed on Sep. 19, 2012.

(51) Int. Cl.
*A61M 1/00* (2006.01)
*G01N 1/18* (2006.01)
*A61M 1/02* (2006.01)
*A61B 5/15* (2006.01)

(52) U.S. Cl.
CPC ............ *G01N 1/18* (2013.01); *A61M 1/0231* (2014.02); *A61M 1/0236* (2014.02); *A61B 5/150992* (2013.01)

(58) Field of Classification Search
CPC .......... A61M 1/0236; A61B 5/150992; F04B 43/12; G01N 1/18; G01N 33/48
See application file for complete search history.

(56) References Cited

U.S. PATENT DOCUMENTS

| | | | |
|---|---|---|---|
| 5,868,696 A | 2/1999 | Giesler et al. | |
| 6,027,938 A * | 2/2000 | Barnes et al. | 435/392 |
| 2004/0009542 A1 * | 1/2004 | Dumont et al. | 435/7.32 |
| 2011/0139276 A1 * | 6/2011 | Kashmiran et al. | 137/561 R |
| 2013/0029411 A1 * | 1/2013 | Roy et al. | 435/325 |

* cited by examiner

*Primary Examiner* — Tatyana Zalukaeva
*Assistant Examiner* — Benjamin Klein
(74) *Attorney, Agent, or Firm* — Cook Alex, Ltd.

(57) ABSTRACT

A blood component sampling system and method are disclosed. The system is pre-connected and includes a collected blood component container and a reservoir having substantially fixed volume and at least one volumetric indicator indicating a selected volume and a sample container docking station configured to cooperate with a sample collection container. The system and method provide ease of sampling with reduced risk of contamination.

17 Claims, 4 Drawing Sheets

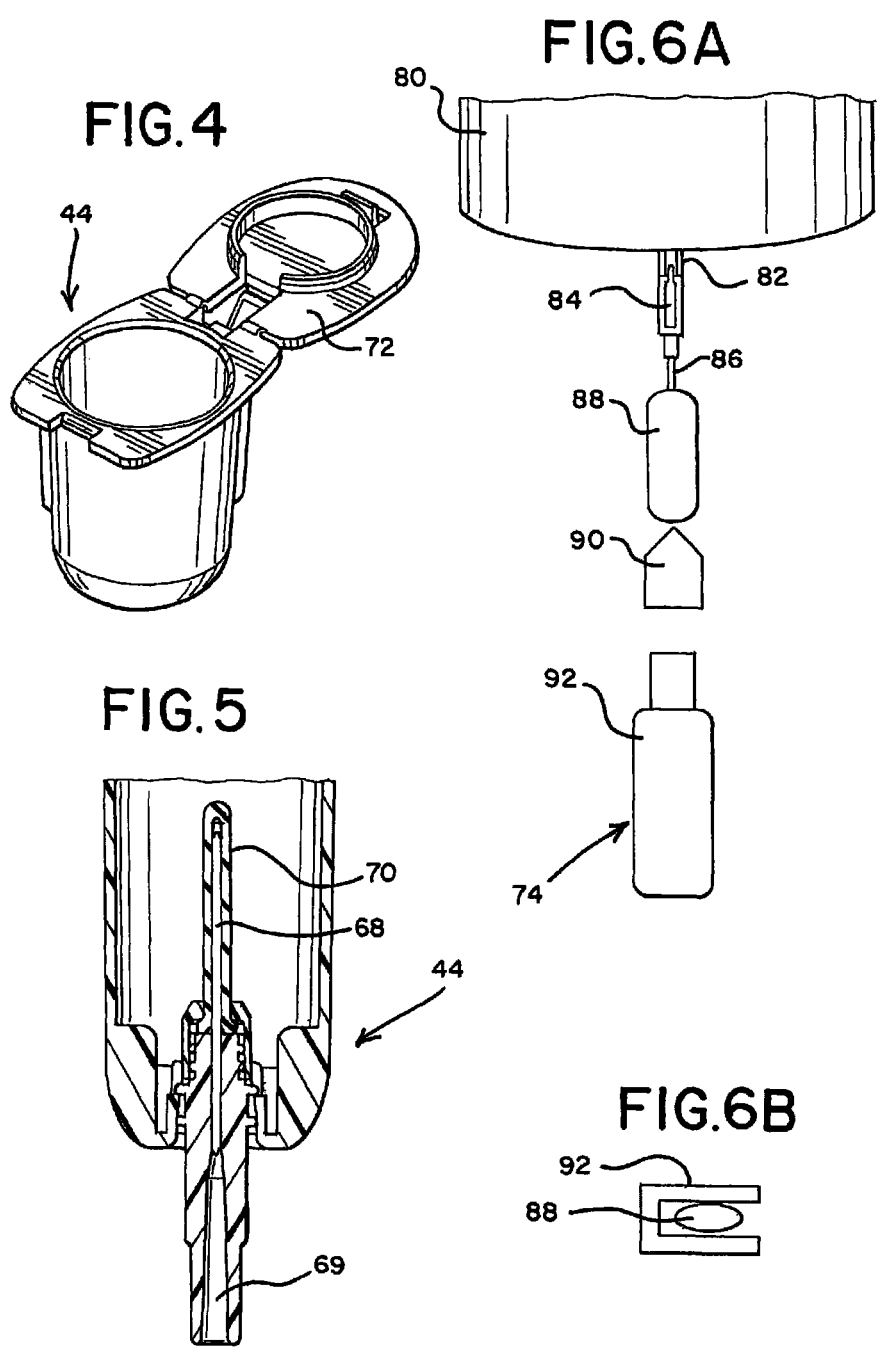

BLOOD COMPONENT SAMPLING SYSTEM AND BLOOD PROCESSING SYSTEMS AND METHODS EMPLOYING SAME

This application claims priority to and the benefit of U.S. Provisional Patent Application No. 61/702,924, filed Sep. 19, 2012, which is hereby also incorporated by reference herein.

FIELD OF THE DISCLOSURE

The present subject matter relates to blood processing systems and, more particularly, to a blood component sampling system and to blood processing systems and methods employing a blood component sampling system.

DESCRIPTION OF RELATED ART

Whole blood is routinely separated into its various components, such as red blood cells, platelets, and plasma during or after collection from donors. This is sometimes carried out manually, typically by collecting a unit of whole blood from a donor and then processing it at a different location to separate the whole blood into desired components. Often, however, the process is carried out using automated or semi-automated blood separation (or apheresis) devices, which separate and collect one or more desired components from whole blood and return the remaining components to the donor. Typical apheresis devices employ reusable durable devices or equipment based on centrifugation or other separation principles, in combination with single use, sterile blood processing sets or flow circuits.

As noted above, these devices often target one or more specific blood components such as platelets or red cells and return the remaining components. Red cells are often used in the treatment of trauma injuries. Platelets are often used for administration to cancer patients undergoing treatment that suppresses the ability of the body to generate new cells. Platelets, which are among the shortest lived blood cell, are critical to blood clotting and cancer patients often require repeated administration of platelets. Because platelets are usually stored at about room temperature, which is conducive to the growth of bacteria, testing of collected platelets is routinely carried out for bacterial contamination. In the past, such testing has been carried out with a variety of equipment and devices, such as syringes and the like for withdrawing samples from the platelet collection container. This is workable, but has a number of shortcomings, and there is a continuing need for products and methods which are conducive to efficient, reliable testing without creating undue risk of contamination during the testing process.

The present subject matter is described for exemplary purposes only with reference to the AMICUS® apheresis system marketed by Fenwal, Inc. of Lake Zurich, Ill. One version of the AMICUS® system is described in greater detail in U.S. Pat. No. 5,868,696, which is hereby incorporated herein by reference. However, the reference to the Amicus system is for purpose of illustration and not limitation. The present subject matter is also applicable to apheresis/collection systems from other manufacturers, and may be used with other blood components, including whole blood, as well.

SUMMARY

There are several aspects of the present subject matter that may be embodied separately or together in the devices, systems and methods described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a pre-assembled sterile blood component sampling system comprises a collected blood component container, at least one reservoir having a substantially fixed volume with at least one volumetric indicator indicating a selected volume within the reservoir and a sample container docking station configured to cooperate with a sample collection container. In systems requiring venting of residual or displacement air, such as a system employing a rigid reservoir, the reservoir may also include a vent opening for the flow of displacement air therethrough and the system may include a sterile filter disposed between the vent opening and the ambient atmosphere to filter any air passing therethrough. In this aspect, a first fluid flow path selectively communicates between the blood component container and the at least one reservoir, and a second fluid flow path selectively communicates between the at least one reservoir and the docking station. Therefore, a blood component sample of selected volume may be transferred from the collected blood component container to the reservoir and from the reservoir to docking station for withdrawal into a sample collection container.

In another aspect, a method of blood component retrieval from a collected blood component container comprises flowing blood component through a sterile closed fluid flow path into a reservoir having a substantially fixed volume and at least one volumetric indicator indicating a selected volume until the selected volume amount is in the reservoir, closing the fluid flow path between the reservoir and blood component container, and flowing the selected volume of blood component from reservoir through a closed fluid flow path communicating with a sample container docking station and into a separate sample collection container.

BRIEF DESCRIPTION OF THE DRAWINGS

FIG. 4 is a perspective view of a sample container docking station employed in the disposable sampling system of FIG. 3.

FIG. 5 is a cross-sectional view of the lower portion of the docking system, illustrating the fluid connection port and a covered piercing needle or spike.

FIG. 6A is a plan view of another embodiment of a sampling system in accordance with the subject matter, and FIG. 6B is a side view of a flexible reservoir (sample chamber) and restraining fixture.

DESCRIPTION OF THE ILLUSTRATED EMBODIMENTS

The embodiments disclosed herein are for the purpose of providing the required description of the present subject matter. They are only exemplary, and the present subject matter may be embodied in various forms and employed with various blood processing or apheresis systems. Therefore, specific details disclosed herein are not to be interpreted as limiting the subject matter defined in the accompanying claims.

Figure 1:
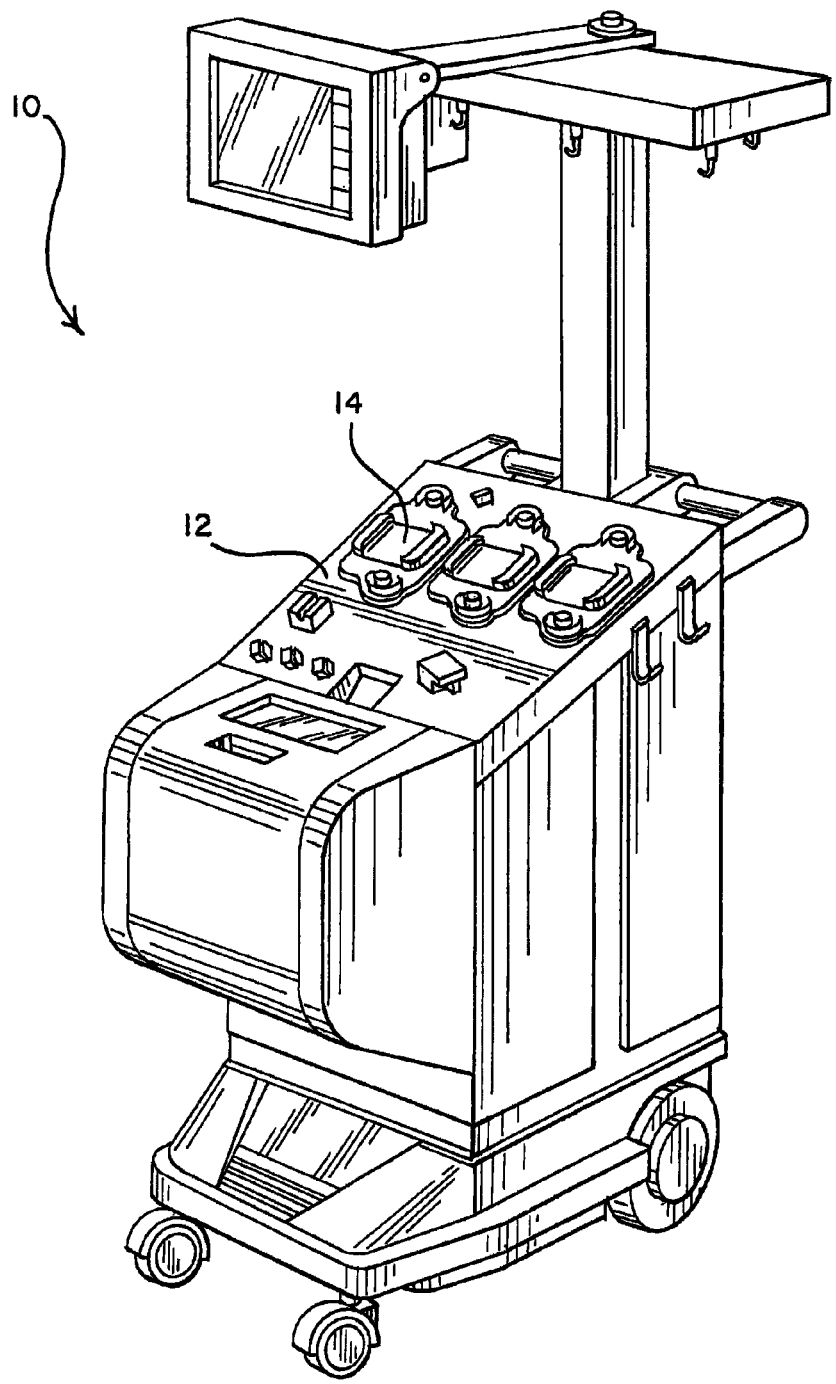
FIG. 1 is a perspective view of an exemplary durable fluid (e.g., blood) processing centrifuge system that may be used in combination with a preassembled sterile fluid flow circuit according to the present disclosure.

FIG. 1 shows a well known durable centrifugal fluid processing (apheresis) device or system 10 that may be used in combination with the sampling system and methods according to the present disclosure. The system is currently marketed as the AMICUS® separator by Fenwal, Inc. of Lake Zurich, Ill. The system 10 can be used for processing various fluids, but is particularly well suited for processing whole blood and other suspensions of biological cellular materials. The system 10 includes a centrifuge chamber (not visible in FIG. 1) suitable for separating a fluid such as blood into its components (e.g. red cells, plasma and platelets) based on the density of such components. A more detailed description of the centrifuge and the other elements of the system 10 can be found in U.S. Pat. No. 5,868,696, which is incorporated by reference herein. While various aspects of the present disclosure will be described in the context of their use with the system 10 of FIG. 1, it should be understood that the sampling system and method described herein may be used in other blood separation systems and devices such as, but not limited to, the Fenwal Alyx® and CS3000® systems, the Caridian BCT Spectra® and Trima® systems, and the Haemonetics MCS® device and other such systems.

Turning back to the Amicus separator of FIG. 1, the device has a sloped front panel 12 that includes at least one cassette holder 14 and assorted sensors and valves. The cassette holder 14 is configured to receive a fluid processing cassette 16 (FIG. 2) of a disposable, single use processing set. An exemplary processing set that is suitable for use in the system 10 of FIG. 1 can be found in FIG. 2 and in U.S. Pat. No. 5,868,696 incorporated by reference herein.

Figure 2:
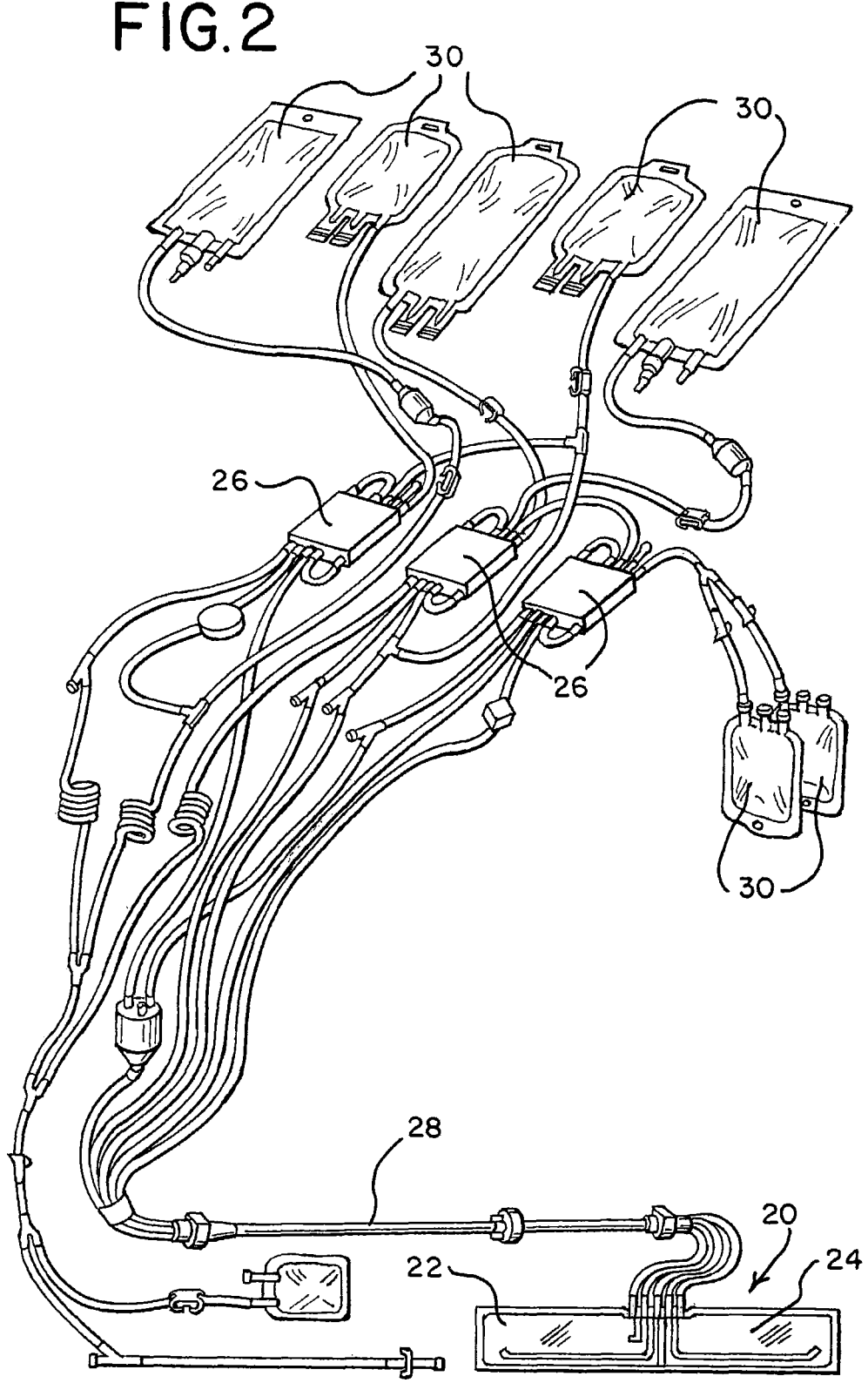
FIG. 2 is a perspective view of a preassembled sterile fluid flow circuit that has been used with the system of FIG. 1 and may be used in combination with the sampling system and method of the present disclosure.

FIG. 2 shows an exploded view of a pre-assembled and sterilized disposable processing assembly or fluid circuit 18 that is usable in association with the centrifuge assembly 10. The assembly 18 includes a flexible plastic processing chamber 20, and in use, the centrifuge assembly 10 rotates the processing chamber 18 within a rotating bowl or channel to centrifugally separate blood components. The construction of the processing chamber 20 can vary. As illustrated, the chamber is for two stage separation procedures, such as where red cells are separated from platelet-rich plasma in a first separation stage or compartment 22 and platelets are concentrated from the platelet-rich plasma in a second separation stage or compartment 24. The processing assembly 18 includes an array of flexible tubing that forms a closed fluid circuit that conveys liquids to and from the processing chamber 20.

The fluid circuit 18 includes a number of containers 30. In use, the containers 30 fit on hangers on the centrifuge assembly 12 (see FIG. 2) to dispense and receive liquids during processing. The fluid circuit 18 also includes one or more flow control cassettes, designated 26A; 26B; and 26C that serve, in association with pump and valve stations on the centrifuge assembly 10, to direct liquid flow among the multiple liquid sources and destinations during a blood processing procedure.

A portion of the fluid circuit 18 leading between the cassettes 26 and the processing chamber 20 is bundled together to form an umbilicus 28. The umbilicus 28 links the rotating parts of the processing assembly 18 (principally the processing chamber 20) with the nonrotating, stationary part of the processing assembly 18 (principally the cassettes 26, containers 30 and related tubing).

One significant use of the Amicus separator is to separate and collect platelets from the blood of a healthy donor for later therapeutic administration to a patient. In that process the platelets are concentrated in the second stage or compartment 24 of processing chamber 20. The concentrated platelets may be retained in the second separation compartment or re-suspended and transferred to a separate storage container. In other separation or apheresis systems, platelet concentrate may be collected directly into a storage container. As noted earlier, platelets are usually stored at about room temperatures, and are routinely tested for bacterial contamination.

Figure 3:
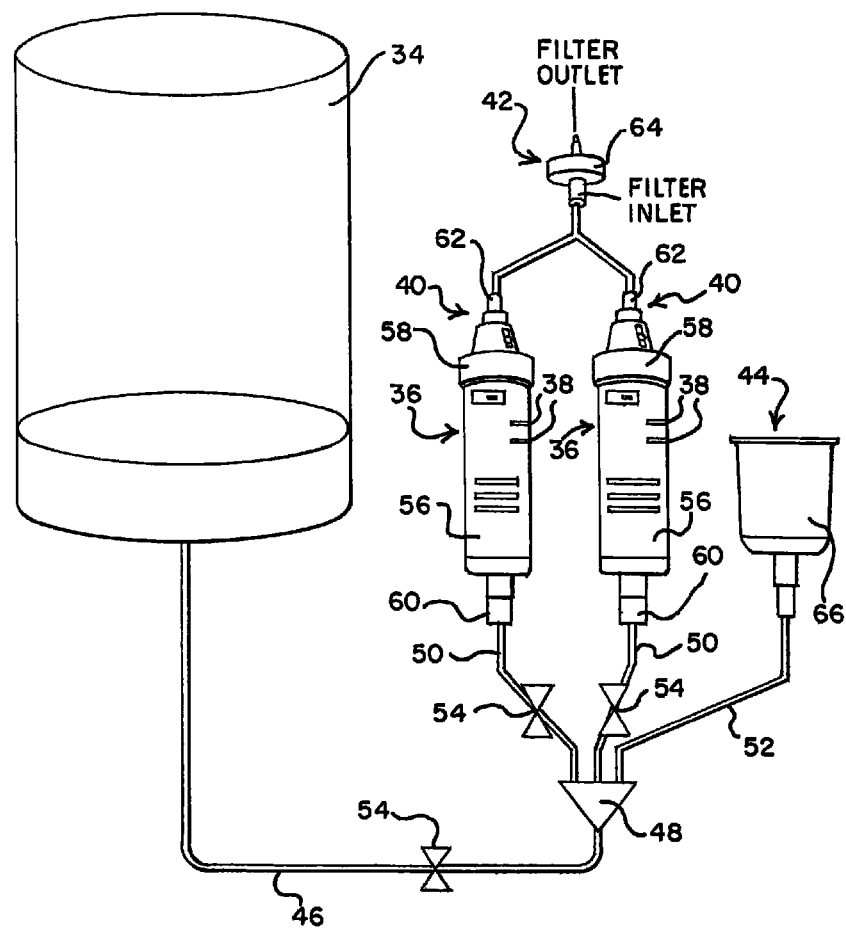
FIG. 3 is a plan view of a sampling system in accordance with this disclosure that may be used in combination with the fluid processing system of FIG. 1 and the fluid flow circuit of FIG. 2.

FIG. 3 illustrates an example of a preassembled sterile sampling assembly or subassembly 32 that may be pre-connected as part of the sterile disposable processing circuit 18 and employed in connection with bacterial testing. One of the illustrated components of the sampling assembly is a collected platelet storage container 34. This container may, for example, be the second separation compartment 24 of the processing chamber or a separate storage container, such as one of containers 30. Of course, the present subject matter is not limited to use with a platelets only, but may be used with whole blood or with other component collections, such as concentrated red cells or plasma, where testing is desired. Accordingly, as used in this description, unless otherwise specified, "blood component" includes whole blood, red cells and red cell concentrate, platelets and platelet concentrate, plasma and/or other elements of blood.

As shown in FIG. 3, in addition to the collected blood component container 34, the sampling assembly or sub-assembly 32 includes at least one reservoir or sample chamber 36 of substantially fixed volume having at least one volumetric indicator or indicia 38 and a vent opening 40 for flow of displacement air into the reservoir, a sterile filter 42 to filter air passing into the reservoir, and a sample container docking station 44. These components are interconnected by flexible plastic tubing or other suitable flow conduits. More specifically, tubing or other conduit 46, extends from a port on the bottom of the collected blood component container 34 to a three way connector 48 from the three way connector. Tubing or other conduit 50 extends from the three way connector to each of the illustrated reservoirs 36, and tubing or conduit 52 extends from the three way connector to the sample container docking station 44. Conduits 46 and 50 are each preferably controlled by a flow control clamp 54 for manual control of flow through the particular tubing or conduit. As noted earlier, the entire sampling assembly or subassembly 32 is preferably preassembled and sterilized and part of the preassembled and pre-sterilized disposable fluid processing circuit 18, or it may be separately provided and sterilely attached to the processing circuit 18 before or after blood component collection, if desired.

As noted above, the collected blood component container 34 may be of any suitable design or configuration, but will typically comprise a flexible plastic container of material suitable for storage of the particular blood component in question. The collected blood component 34 may remain attached to the larger disposable fluid processing circuit or, more typically, is sealed and separated from the larger fluid processing circuit after the target blood component is collected. Preferably, the collected blood component container is pre-attached to the sampling subassembly 32, and an internal frangible closure, as well known in the medical device field, may be provided in the container port to which tubing 46 is attached or may be provided in tubing 46 itself so that the container is fully sealed until access is desired, at which time the frangible closure is opened by manual manipulation of the port or tubing. It should be noted that the collected blood component container and blood component therein may also be the result of a manual collection process where collected platelets from multiple donors are pooled together into a single dose and stored in the blood component container.

The reservoir 36 has a substantially fixed volume, and in one embodiment may be a rigid container of fixed volume for receiving a selected sample quantity of fluid from the collected component container. As illustrated in FIG. 3, the sampling subassembly includes two reservoirs 36, although one or more reservoirs may be employed as desired. For example, two or more reservoirs may be desired if a particularly large volume of blood component is collected in the container 34, such as a double or triple dose of platelet concentrate. Alternatively, a single reservoir may be used multiple times for multiple samples if desired.

As illustrated in FIG. 3, the reservoir has a substantially clear rigid plastic housing 56 which allows ease of user viewing of the contents. The housing is closed at the upper end by cap 58. The reservoir housing 56 has a bottom inlet opening or port 60 for receiving a fluid sample from the collected blood component container 34 and for dispensing a sample to the docking station 44, and the cap 58 has a vent opening or port 62 for allowing displacement air to exit or enter the reservoir.

For indicating the volume of sample fluid withdrawn into the reservoir from the collected blood component container, the reservoir includes one or more volumetric indicators or indicia 38 that provide a visual indication to the user of the volume of sample within the reservoir. In the illustrated embodiment, the reservoir has two volumetric indicators (e.g. fill lines or numeric indicators) indicating different volumetric levels such as minimum or maximum or simply different volumetric levels. This allows the subassembly to accommodate different bacterial testing systems that often require different sample sizes for testing. In some situations the sampling system may require a minimum sample size, and other systems may require a sample size between minimum and maximum quantities and other sampling systems simply require different sample sizes. For example, a testing system may require a sample volume of not less than 8 ml for accuracy and resolution, but not greater than 10 ml so as to avoid false positives. Also, withdrawing more blood component than is needed wastes valuable blood component. Accordingly, the volumetric indicator 38 on the reservoir preferably accommodates a variety of a sampling system that may be employed by the end user. Without limiting the foregoing, one well known bacterial testing system with which the illustrated sampling assembly may be used is the BacT/ALERT microbial detection system from Biomerieux, Inc. of Durham, N.C.

Although the reservoir 36 is preferably rigid with fixed internal volume, the reservoir may also be of flexible plastic material, such as a bag or pouch, which is constrained so that it provides a substantially fixed volume that varies only within allowable error. For example, such a reservoir may include a rigid outer sleeve, pouch, frame or fixture that constrains the expansion the flexible reservoir to the desired substantially fixed volume. Alternatively, the reservoir, if made of flexible plastic material may include constraining structures, such as a flexible but non-extensible ribbons, fibers or mesh, adhered to the reservoir to limit its filled expansion to the substantially desired volume. A flexible reservoir may not require venting, but if venting of residual or displacement air is required, a sterile filter and vent port arrangement such as described earlier may be employed.

To maintain sterility while allowing gas to exit the reservoir 36 when it is being filled and displacement gas to enter when it is being emptied, the sterilizing filter 64 is attachment to the upper vent 40 of the reservoir so that any venting or displacement gas must pass through the filter. The filter 64 may be of any suitable construction but, as illustrated, includes a rigid plastic housing having an inlet, (in sealed attachment to reservoir vent opening 62) an outlet to the ambient atmosphere and a sterilizing filter media located internally of the housing and between the inlet and the outlet. Such a sterile filter media may be, for example a 0.2 or 0.22 micron antimicrobial membrane filter of type well known and commonly available from manufacturers such as Pall Corporation and others.

As noted earlier, the sample blood component is drawn from the reservoirs 36 into the sample container docking station 44. One version of a docking station is illustrated in FIGS. 4 and 5. The docking station 44 shown there includes a sample barrel or housing 66 for receiving a vacuum-charged container such as a BacT/ALERT sample container, for drawing the blood component sample from the reservoir. As illustrated in FIG. 5, the docking station may include a hollow piercing needle or spike 68 that extends upwardly from the floor of the sample barrel 66 and is in fluid communication with bottom inlet port 69 of the sample barrel. The needle is preferably covered by a flexible, piercable sleeve 70 and the upper open end of the barrel is closable by a cover 72 hingedly connected to the barrel and including a releasable locking feature or arrangement.

In use, a vacuum-charged sample container 74 is inserted into the sample barrel 66 of the docking station 44. At the end of the sample container is a piercable diaphragm or septum, and as the sample container is inserted into the barrel, the needle or piercing pin cover 72 is forced downwardly past the piercing end, and the needle or spike 68 pierces the diaphragm or septum of the sample container. The vacuum in the container then draws the fluid sample from the reservoir into the sample container. Because the reservoir is of substantially fixed volume, the user can be better assured that the quantities required for the particular bacterial testing system will be satisfied without undue risk of inadvertent contamination. Further, unduly large amount of valuable blood component will not be withdrawn for testing purposes, reducing unnecessary waste.

In connection with providing relative precise quantities of blood component for testing purposes, it should be understood that if a small residual amount of blood component remains in tubing 46 between clamp 54 and three-way connector 48 and in tubing 50 between the three way connector and reservoir(s), such quantities may be accounted for in the location of the volumetric indicator 38 on the reservoir, so that the desired volume drawn into the sample container is the sum of the reservoir volume and tubing-contained quantities. Also, to better assure reproducibility, if tubing-contained quantities are sufficiently large to require consideration, the length of tubing 50 and tubing 46 downstream of clamp 54 may be fixed and controlled during production to limit variation between different sampling subassemblies.

Method of Use

The sampling assembly or subassembly 32 may be used to provide reliable volumetric fluid samples for bacterial testing with reduced risk of contamination and while avoiding unnecessary waste of valuable collected blood component as described below. Assuming, for purposes of discussion, that the collected blood component container 34 has been a sealed and separated from the remainder of the blood processing circuit 18 and remains attached to the sampling subassembly 32, to transfer a selected sample from the collected component container 34 to one or more of the reservoirs 36, the collected blood component container is preferably raised to a height above the reservoir 36. Clamp 54 on tubing conduit 46 is then opened and one of the clamps 54 on one of the tubing conduits 50 to the selected reservoir is also opened. As a result, flow of blood component from the blood component collection container is allowed under gravitational force into the selected reservoir. The flow rate may be controlled by varying the degree of occlusion of either the clamp on the tubing 46 or the clamp on the tubing 50 leading to the selected reservoir. The reservoir is filled to the desired level as will be readily visually evident to the user from the volumetric indicator 30 on the reservoir. At that point, the clamp 54 on the tubing extending from the three way connector to the reservoir may be closed or, alternatively, clamp 54 on the unfilled reservoir may be opened to allow sterile extraction of an additional sample aliquot from the collection container into the second reservoir in the manner described above. At the completion of filling of the reservoir or reservoirs, the clamps between the collected blood component container and the three way connector and between the three way connector and the reservoirs are closed.

As the reservoirs are filled with blood component, air or gas escaping from the reservoirs must pass through the sterilizing filter 64 and, similarly, as described later, as sample flows from the reservoir to the sample container docking station the sterilizing filter allows sterile displacement air to enter the reservoir for complete emptying. After the sample reservoirs are filled, the reservoirs 36 may be disconnected from the collected blood component container 34, if desired, by sealing and severing the tubing or conduit 46 that extends between the collection container and the three way connector 48.

For transferring the contents of the reservoir to the sample container docking station, the reservoir and the docking station are each preferably maintained in a generally vertical orientation. The clamp 54 on the tubing conduit 50 of the selected reservoir is opened and the sample bottle is pushed into the barrel of the docking station 44, causing the piercing pin or needle 68 to pierce the diaphragm or the septum of the sample container. Due to the vacuum in the sample container, the fluid in the reservoir will flow through the conduit 46, through the three way connector 48 and through the conduit 50 into the inlet port 69 of the docking station, through the piercing spike or needle 68 and into the sample container. After the sample is withdrawn, the sample container may be removed from the docking station. Sleeve 70 will recover the needle 67 and cover 72 can be closed over the open end of sample barrel 66 to reduce contamination risk.

If it is desired at the time to remove the sample that was collected in the second of the illustrated reservoirs, the first sample collection container may be withdrawn from the docking station and a fresh, vacuum charged container inserted and similar steps carried out to allow flow from the selected reservoir into the additional collection container.

Another Embodiment

FIGS. 6A and 6B show further embodiments of the present subject matter. FIG. 6A illustrates a pre-attached sampling assembly or subassembly including a collected blood component container 80 having a bottom end port 82 containing a frangible connector 84. The port 82 is pre-connected via tubing 86 to a single sample container or reservoir 88 which is pre-connected to a sample container docking station 90 suitable for use with one or more sample collection containers, such as a BacT/ALERT container 92.

FIG. 6B illustrates, in side view, a generally u-shaped frame or fixture 92 as one type of restraining structure that could be used in the event the reservoir 88 is made of flexible material. The fixture may be sized to meet particular user requirements. For example, different users and/or different testing systems may require that different blood or blood component volumes be drawn for test purposes. In the embodiment in FIG. 6B, restraining fixtures of different sizes or of an adjustable size may be provided to limit/control the volume of the sample withdrawn into a flexible reservoir 88 to that required by the particular user or testing system. The fixture may also have visible indicia of different volumes, such as minimum and maximum, that provides direct volumetric indication to the user, particularly when the flexible reservoir is clear.

In summary, as a consequence of the construction and operation of the sampling subassembly, it may be seen that relatively precise predictable quantities of blood component samples may be withdrawn for testing with reliable amounts of the volumes necessary for testing and without risking a breach of sterility by reason of unnecessary or repeated connections or disconnections of the reservoirs or sampling containers from the system.

The invention claimed is:

1. A pre-connected sterile blood component sampling system comprising:
   a collected blood component container;
   at least one reservoir having a substantially fixed volume, and including opposed ends and a side wall extending between the ends and at least one volumetric indicator located on the side wall of the reservoir and indicating a selected volume;
   a sample container docking station configured to cooperate with a sample collection container;
   a first fluid flow path selectively communicating between the blood component container and through one end of the at least one reservoir, and wherein the location of the volumetric indicator on the side wall of the reservoir is at a position corresponding to an internal volume of the reservoir between the one end and the position of the indicator that is equal to the selected volume minus a volume of at least a portion of the first fluid flow path whereby the selected volume indicated by the volumetric indicator takes into account the volume of blood component residing in the at least a portion of the first fluid flow path;
   a second fluid flow path selectively communicating between the one end of the at least one reservoir and the docking station; and
   whereby a blood component sample of selected volume may be transferred from the collected blood component container and the first fluid flow path to the docking station for withdrawal into a sample collection container.

2. The system of claim 1 further comprising a blood processing circuit for separating the collected blood component from whole blood.

3. The system of claim 1 wherein the at least one reservoir comprises a rigid container.

4. The system of claim 1 wherein the at least one reservoir comprises a flexible container including a separate constraint that substantially fixes the maximum volume of the container by limiting expansion of the container.

5. The system of claim 1 further comprising a first flow path valve in cooperative association with the first fluid flow path between the blood component container and the at least one reservoir.

6. The system of claim 5 further comprising a second flow path valve in cooperative association with the second fluid flow path between the at least one reservoir and the sample container docking station.

7. The system of claim 1 in which the location of the volumetric indicator on the side wall of the reservoir is at a position corresponding to an internal volume of the reservoir between the one end and the position of the indicator that is substantially equal to a volume corresponding to one or more selected volumetric sample sizes minus the volume of blood component residing in the at least a portion of the first fluid flow path.

8. The system of claim 1 wherein the at least one reservoir includes a vent opening for flow of gas therethrough and the system includes a sterile filter disposed between the vent opening and ambient atmosphere to filter any gas passing therethrough.

9. The system of claim 1 in which the at least one reservoir comprises a plurality of said reservoirs in fluid communication with the same blood component container.

10. A method of blood component retrieval from a collected blood component container into a reservoir, which reservoir has a substantially fixed volume and includes opposed ends, a side wall extending between the ends and at least one volumetric indicator located on the side wall, the location of the volumetric indicator on the side wall of the reservoir being at a position corresponding to an internal volume of the reservoir between one end of the reservoir and the position of the volumetric indicator that is equal to a selected volume minus a flow path residual volume, the method comprising:
flowing blood component from the collected blood component container through a sterile closed fluid flow path into the reservoir through the one end thereof until the quantity of blood component in the reservoir reaches the level of the volumetric indicator and a quantity of blood component substantially equal to the flow path residual volume remains in a portion of the flow path;
closing the fluid flow path between the reservoir and blood component container; and
flowing the selected volume of blood component from the reservoir and the fluid flow path through a closed fluid flow path communicating with a sample container docking station and into a separate sample collection container.

11. The method of claim 10 including venting displacement air from the reservoir through a sterile filter during the flowing of blood component into the reservoir and venting displacement air into the reservoir through a sterile filter during the flowing of blood component from the reservoir.

12. A pre-connected sterile blood component sampling system comprising:
a collected blood component container including an upper end configured for hanging the container and a lower end;
at least two substantially rigid reservoirs, each having opposed upper and lower ends and a side wall extending between reservoir upper and lower ends, a substantially fixed volume, and at least one volumetric indicator located on the side wall of each reservoir and indicating a selected volume, the location of the volumetric indicator on the side wall of the reservoir being at a position corresponding to an internal volume of the reservoir between the lower end of the reservoir and the position of the volumetric indicator that is equal to the selected volume minus a volume of at least a portion of the fluid flow path;
a sample container docking station configured to cooperate with a sample collection container;
a first fluid flow path selectively communicating between the lower end of the blood component container and through the lower end of each reservoir;
a second fluid flow path selectively communicating between the lower end of each reservoir and the docking station;
a vent including a sterile filter comprising an antimicrobial filter media communicating between the ambient atmosphere and the reservoir through the upper end of each reservoir, and
whereby a blood component sample of selected volume may be transferred from the collected blood component container, the sterile filter allowing air to flow from the reservoir through the antimicrobial filter media into the ambient atmosphere during blood component inflow into the reservoir, and the selected volume of blood component may be transferred from each reservoir and the first fluid flow path to the docking station for withdrawal into a sample collection container, the sterile filter allowing air to flow through the antimicrobial filter media into the respective reservoir from the ambient atmosphere during blood component outflow from the reservoir.

13. The system of claim 12 further comprising a blood processing circuit for separating the collected blood component from whole blood.

14. The system of claim 12 further comprising a first flow path valve in cooperative association with the first fluid flow path between the blood component container and each reservoir.

15. The system of claim 14 further comprising a second flow path valve in cooperative association with second fluid flow path between each reservoir and the sample container docking station.

16. The system of claim 12 in which the location of the volumetric indicator on the side wall of each reservoir is at a position corresponding to an internal volume of the reservoir between the lower end of the reservoir and the position of the indicator that is substantially equal to a volume corresponding to one or more selected volumetric sample sizes minus the volume of blood component residing in at least a portion of the first fluid flow path.

17. The system of claim 12 in which the at least two reservoirs are individually separable from the blood component container.

* * * * *